(12) United States Patent
Phillips et al.

(10) Patent No.: US 7,199,228 B2
(45) Date of Patent: Apr. 3, 2007

(54) OLIGONUCLEOTIDE COMPOSITIONS AND THEIR USE TO INDUCE APOPTOSIS

(75) Inventors: Nigel C. Phillips, Pointe-Claire (CA); Mario C. Filion, Laval (CA); Zdenek Richard Holan, Montreal (CA); Stéphanie Reader, Ste-Julie (CA)

(73) Assignee: Bioniche Life Sciences, Inc, Belleville, Ontario (CA)

( * ) Notice: Subject to any disclaimer, the term of this patent is extended or adjusted under 35 U.S.C. 154(b) by 592 days.

(21) Appl. No.: 10/223,672

(22) Filed: Aug. 19, 2002

(65) Prior Publication Data

US 2003/0113763 A1 Jun. 19, 2003

Related U.S. Application Data

(60) Provisional application No. 60/313,290, filed on Aug. 17, 2001.

(51) Int. Cl.
C07H 21/04 (2006.01)
A61K 31/70 (2006.01)
C12Q 1/68 (2006.01)

(52) U.S. Cl. ............ 536/23.1; 536/24.5; 514/44; 435/6

(58) Field of Classification Search .......... None
See application file for complete search history.

(56) References Cited

U.S. PATENT DOCUMENTS 5,106,727 A * 4/1992 Hartley et al. .......... 435/6

FOREIGN PATENT DOCUMENTS

WO WO 9318187 A1 * 9/1993

OTHER PUBLICATIONS

Eritja et al. (1986) Nucleic Acids Res. 14:8135-8153.*
Jiricny et al. (1986) Nucleic Acids Res. 14:6579-6590.*
Bronwyn G. Hughes and Roland K. Robins; 2',5'-Oligoadenylates and Related 2',5'-Oligonucleotide Analogues. 2. Effect on Cellular Proliferation, Protein Synthesis, and Endoribonuclease Activity; Biochemistry (1983) 22, 2127-2135.
David Wang and John M. Essigmann; Kinetics of Oxidized Cytosine Repair by Endonuclease III of Escherichia coli; Biochemistry (1997), 36, 8628-8633.
Ramon Eritja et al.; Synthesis and properties of oligonucleotides containing 2'-deoxynebularine and 2'-deoxyxanthosine; Nucleic Acids Research; (1986) vol. 14, No. 20; 8135-8153.
Dietmar Porschke; Thermodynamic and Kinetic Parameters of Oligonucleotide—Oligopeptide Interactions Specificity of Arginine inosine Association' Eur. J. Biochem; (1978) 86, 291-299.

Murat Saparbaev and Jacques Laval; Excision of hypoxanthine from DNA containing dIMP residues by the Escherichia coli, yeast, rat, and human alkylpurine; Proc. Natl. Acad. Sci. USA; (1994) vol. 91, p. 5873-5877.
Paula J. Bates et al.; Antiproliferative Activity of G-rich Oligonucleotides Correlates with Protein Binding; The Journal of Biological Chemistry; vol. 274, No. 37, Issue of Sep. 10, pp. 26369-26377, 1999.
Goberdhan P. Dimri et al.; A biomarker that identifies senescent human cells in culture and in aging skin in vitro; Proc. Natl. Acad. Sci. USA; vol. 92, pp. 9363-9367; Sep. 1995; Cell Biology.
M.C. Filion, Ph.D. et al.; Pro-apoptotic and terminal differentiation activity of a 6 base length phosphodiester oligonucleotide, Oligomodulator BT 99-25, towards leukemia cells.; (oral session 1092) Program and Abstracts of the 6th International Symposium held at L'Institut Pasteur, Paris, France; Feb. 9-12, 2002.
John E. Mata et al.; A Hexameric Phosphorothioate Oligonucleotide Telomerase Inhibitor Arrests Growth of Burkitt's Lymphoma Cells in Vitro and in Vivo; Toxicology and Applied Pharmacology 144; pp. 189-197 (1997); Article No. TO978103.
Carla Morassutti et al.; Effect of Oligomer Length and Base Substitutions on the Cytotoxic Activity and Specific Nuclear Protein Recognition of GTn Oligonucleotides in the Human Leukemic CCRF-CEM Cell Line; Nucleosides & Nucleotides, 18(6&7), 1711-1716 (1999).
Martin Read et al.; Structure-based design of selective and potent G quadruplux-mediated telomerase inhibitors; PNAS, 4844-4849; Apr. 24, 2001, vol. 98, No. 9.
Bruna Scaggiante et al.; Human cancer cell lines growth inhibition by GTn oligodeoxyribonucleotides recognizing single-stranded DNA-binding proteins; Department of Biomedical Sciences and Technologies and Department of Bone Marrow Transplant, University of Udine, Italy, (Received Nov. 28, 1997)—EJB 97 1675/2.
Richard W. Wagner; Gene inhibition using antisense oligodeoxynucleotides; Nature International Weekly Journal of Science; vol. 372, No. 6504, Nov. 24, 1994; 333-335.
Valentin V. Vlassov et al.; Transport of oligonucleotides across natural and model membranes; Biochimica et Biophysica Acta; vol. 1197, No. 1, (1994) 95-108.

* cited by examiner

Primary Examiner—Sean McGarry
Assistant Examiner—Louis Wollenberger
(74) Attorney, Agent, or Firm—Kilpatrick Stockton, LLP

(57) ABSTRACT

The present invention provides novel synthetic oligonucleotide sequences (hereinafter sequence) of 3 to 9 bases in length comprising one or more non-DNA bases wherein the bases are nebularine, hypoxanthine, or uracil, or combinations of nebularine, hypoxanthine and uracil bases. These sequences optionally further comprise one or more guanine bases or one or more thymine bases, or combinations thereof. The present invention also provides methods of using these compositions to induce responses in cells, and to treat diseases and conditions characterized by undesired cellular proliferation such as autoimmune disease, lymphoproliferative disease, inflammation or cancer.

3 Claims, No Drawings

OLIGONUCLEOTIDE COMPOSITIONS AND THEIR USE TO INDUCE APOPTOSIS

PRIOR RELATED APPLICATIONS

The present application claims priority to U.S. Provisional patent application Ser. No. 60/313,290 filed Aug. 17, 2001.

FIELD OF THE INVENTION

The present invention relates to novel oligonucleotide compositions and methods of using them for alteration of cellular function including the inhibition of cellular proliferation, induction of cell cycle arrest and induction of apoptosis.

BACKGROUND OF THE INVENTION

Proliferation is the culmination of a cell's progression through the cell cycle resulting in the division of one cell into two cells. The five major phases of the cell cycle are $G_0$, $G_1$, S, $G_2$, and M. During the $G_0$, phase, cells are quiescent. Most cells in the body, at one time, are in this stage. During the $G_1$ phase, cells, responding to signals to divide, produce the RNA and the proteins necessary for DNA synthesis. During the S-phase (SE, early S-phase; SM, middle S-phase; and SL, late S-phase) the cells replicate their DNA. During the $G_2$ phase, proteins are elaborated in preparation for cell division. During the mitotic (M) phase, the cell divides into two daughter cells. Alterations in cell cycle progression occur in all cancers and may result from over-expression of genes, mutation of regulatory genes, or abrogation of DNA damage checkpoints (Hochhauser D., Anti-Cancer Chemotherapeutic Agents, 8:903, 1997).

Apoptosis or programmed cell death is the physiological process for the killing and removal of unwanted cells and the mechanism whereby chemotherapeutic agents kill cancer cells. Apoptosis is characterized by distinctive morphological changes within cells that include condensation of nuclear chromatin, cell shrinkage, nuclear disintegration, plasma membrane blebbing, and the formation of membrane-bound apoptotic bodies (Wyllie et al., Int. Rev. Cytol., 68: 251, 1980). The translocation of phosphatidylserine from the inner face of the plasma membrane to the outer face coincides with chromatin condensation and is regarded as a cellular hallmark of apoptosis (Koopman, G. et al., Blood, 84:1415, 1994). The actual mechanism of apoptosis is known to be mediated by the activation of a family of cysteine proteases, known as caspases. However, most prior art anti-cancer therapies, whether directed to induction of apoptosis have proven to be less than adequate for clinical applications. Many of these therapies are inefficient or toxic, have adverse side effects, result in development of drug resistance or immunosensitization, and are debilitating for the recipient. Many diseases or conditions are characterized by undesired cellular proliferation and are know to one of ordinary skill in the medical or veterinary arts. New compositions and methods are needed to treat these diseases and conditions.

Synthetic oligonucleotides are polyanionic sequences that are internalized in cells (Vlassov et al., Biochim. Biophys. Acta, 11197:95, 1994). Synthetic oligonucleotides are reported that bind selectively to nucleic acids (Wagner, R., Nature, 372:333, 1994), to specific cellular proteins (Bates et al., J. Biol. Chem., 274:26369, 1999) and to specific nuclear proteins (Scaggiante et al., Eur. J. Biochem, 252: 207, 1998) in order to inhibit proliferation of cancer cells.

Synthetic 27 base sequences containing guanine (G) and variable amounts of thymine (T) (oligonucleotides GTn) wherein n is $\geq 1$ or $\leq 7$ and wherein the number of bases is $\geq 20$ (Scaggiante et al., Eur. J. Biochem., 252:207, 1998), are reported to inhibit growth of cancer cell lines by sequence specific binding to a 45 kDa nuclear protein, whereas GTn, wherein the number of bases is $\leq 20$, are reported to be inactive against cancer cell lines (Morassutti et al., Nucleosides and Nucleotides, 18:1711, 1999). Two synthetic GT-rich oligonucleotides of 15 and 29 bases with 3' aminoalkyl modifications are reported to form G-quartets that bind to nucleolin and to inhibit proliferation of cancer cell lines (Bates et al., J. Biol. Chem., 274:26369, 1999). The synthetic six base TTAGGG-phosphorothioate, having a sequence identical to that of the mammalian telomere repeat sequence, is reported to inhibit proliferation of Burkitt's lymphoma cells in vitro and in vivo (Mata et al., Toxicol. Applied Pharmacol., 144:189, 1997). However, the synthetic six base TTAGGG-phosphodiester nucleotide is reported to have no anti-telomerase activity (U.S. Pat. No. 5,643,890).

Deoxyribonucleotides with biological activity such as antisense DNA (mRNA binding or triplex-forming DNA) or immunostimulatory CpG motifs are characterized by sequence-specific linear motifs, often stabilized by intramolecular base-pair bonding. Backbone modification, such as phosphorothioate substitution, does not adversely affect and often enhances the activity of these molecules.

We have previously described a composition and method comprising 2 to 20 base 3'-OH, 5'-OH synthetic oligonucleotides selected from the group consisting of $(G_xT_y)_n$, $(T_yG_x)_n$, $a(G_xT_y)_n$, $a(T_yG_x)_n$, $(G_xT_y)_nb$, $(T_yG_x)_nb$, $a(G_xT_y)_nb$, $a(T_yG_x)_nb$, wherein x and y is an integer between 1 and 7, n is an integer between 1 and 12, a and b are one or more As, Cs, Gs or Ts, wherein the sequence is between 2 and 20 bases and wherein the sequence induces a response selected from the group consisting of induction of cell cycle arrest, inhibition of proliferation, induction of caspase activation and induction of apoptosis in a number of cancer cells (PCT CA00/01467, WO 01/44465). These oligonucleotides are not designed to have antisense activity, to block the activity of telomerase or to form a triple helix with DNA. Oligonucleotides having non-DNA bases such as nebularine, hypoxanthine or uracil have not been reported to induce apoptosis.

Most prior art anti-cancer therapies, whether directed to inhibition of proliferation, induction of cell cycle arrest or induction of apoptosis have proven to be less than adequate for clinical applications. Many of these therapies are inefficient or toxic, have significant adverse effects, result in development of drug resistance or immunosensitization, and are debilitating for the recipient.

Therefore, there is a continuing need for novel compositions and methods effective for treating diseases and conditions characterized by undesired cellular proliferation, such as autoimmune disease, lymphoproliferative disease, inflammation and cancer. Such compositions and method are needed to inhibit cellular proliferation, induce cell cycle arrest, and induce apoptosis in cells, particularly in cancer cells.

SUMMARY OF THE INVENTION

The present invention fulfills this need by providing novel synthetic oligonucleotide sequences (hereinafter sequence) of 3 to 9 bases in length comprising one or more nebularine bases, one or more hypoxanthine bases, or one or more uracil bases, or combinations of nebularine, hypoxanthine and uracil bases. These sequences optionally further comprise one or more guanine bases or one or more thymine bases, or combinations thereof.

The present invention also provides methods for using these novel synthetic oligonucleotide sequences by combining them with an acceptable carrier to make a composition, and administering the composition in vitro or in vivo in order to induce a cellular response. Preferably the cellular response is inhibition of cellular proliferation, induction of cell cycle arrest or induction of apoptosis. Preferred cells for inhibition of cellular proliferation, induction of cell cycle arrest or induction of apoptosis are cancer cells.

The present invention provides a method for treating a disease or condition characterized by undesired cellular proliferation comprising administration of a composition comprising a sequence of the present invention and a pharmaceutically acceptable carrier to an animal or human having the disease or condition characterized by undesired cellular proliferation, in an amount effective to treat the disease. Any disease or condition characterized by undesired cellular proliferation may be treated with the compositions of the present invention. Such diseases or conditions characterized by undesired cellular proliferation include, but are not limited to, autoimmune disease, inflammation, lymphoproliferative disease, and cancer.

One or more novel sequences of the present invention may be administered with an acceptable carrier as a composition in vitro or in vivo. Further, the compositions of the present invention may be administered together with one or more therapeutic agent. Such administration of the compositions of the present invention may occur before, during or after administration of one or more therapeutic agents known to one of ordinary skill in the medical or veterinary arts. Any therapeutic agent known to one of ordinary skill in the medical or veterinary arts, and employed to treat diseases, may be used in combination with these novel sequences. Such combinations may permit use of lower dosages of therapeutic agents, thereby decreasing unwanted side effects.

Administration of a composition comprising an effective amount of one or more of the sequences of the present invention to an animal or human is a therapeutic treatment that prevents, treats or eliminates a disease or condition characterized by undesired cellular proliferation. Such diseases and conditions are known to one of skill in the medical or veterinary arts and include, but are not limited to, cancer, inflammation, arthritis, lymphoproliferative disorders, asthma and restenosis of arteries following angioplasty.

Cancers include, but are not limited to, squamous cell carcinoma, fibrosarcoma, sarcoid carcinoma, melanoma, mammary cancer, lung cancer, colorectal cancer, renal cancer, osteosarcoma, cutaneous melanoma, basal cell carcinoma, pancreatic cancer, bladder cancer, brain cancer, ovarian cancer, prostate cancer, leukemia, lymphoma and metastases derived therefrom.

Methods and routes of administration of therapeutic agents to animals and humans known to one of ordinary skill in the art may be employed to administer compositions comprising the sequences of the present invention and a pharmaceutically acceptable carrier.

The unexpected and surprising ability of the oligonucleotide sequences of the present invention to induce a cellular response, and particularly to inhibit cell proliferation, to arrest the cell cycle progression and/or to induce apoptosis in cells addresses a long unfulfilled need in the medical arts and provides an important benefit for animals and humans.

These novel compositions may be used to treat conditions of undesired cellular proliferation in animals and humans, including but not limited to autoimmune disease, arthritis, asthma, restenosis of vessels following angioplasty, lymphoproliferative disease, inflammation and cancer.

Accordingly, it is an object of the invention to provide novel synthetic oligonucleotide sequences (hereinafter sequence) of 3 to 9 bases in length, comprising one or more nebularine bases, one or more hypoxanthine bases, or one or more uracil bases, or combinations of nebularine, hypoxanthine and uracil bases. These sequences optionally further comprise one or more guanine bases or one or more thymine bases, or combinations thereof. Preferably the guanine and thymine bases are phosphodiester bases.

Accordingly, it is an object of the present invention to provide novel compositions that induce a cellular response.

It is an object of the present invention to provide methods of using these compositions to induce a cellular response, wherein the cellular response is inhibition of cellular proliferation, arrest of cell cycle progression, or induction of apoptosis.

A further object of the present invention to provide methods of using these compositions to induce a cellular response, wherein the cellular response is inhibition of cellular proliferation, arrest of cell cycle progression, or induction of apoptosis in cancer cells.

It is another object of the present invention to provide methods of using these compositions to treat disease in an animal or human.

Another object of the present invention to provide these compositions for use in preparation of a medicament for treating disease in an animal or human.

Still another object of the present invention is to provide a method comprising administration of one or more of the compositions of the present invention in an amount effective to treat a disease or condition characterized by undesired cellular proliferation in an animal or human.

Yet another object of the present invention is to provide a method comprising administration of one or more of the compositions of the present invention in an amount effective to treat a disease or condition in an animal or human, wherein the disease or conditions is characterized by undesired cellular proliferation and is an autoimmune disease, inflammation, asthma, a lymphoproliferative disease, restenosis of vessels following angioplasty or cancer.

Still another object of the present invention is to provide a method comprising administration of one or more of the compositions of the present invention before, during or after administration of another therapeutic substance to induce a cellular response.

Yet another object of the present invention is to provide a method comprising administration of one or more of the compositions of the present invention before, during or after administration of another therapeutic substance to induce a cellular response, wherein the cellular response is inhibition of cellular proliferation, arrest of cell cycle progression, or induction of apoptosis in cancer cells.

Still another object of the present invention is to provide a method comprising administration of one or more than one of the compositions of the present invention before, during or after administration of another therapeutic substance to treat a disease in an animal or human, wherein the disease is characterized by undesired cellular proliferation.

Yet another object of the present invention is to provide a method comprising administration of one or more than one of the compositions of the present invention before, during or after administration of another therapeutic substance to treat a disease or condition characterized by undesired cellular proliferation in an animal or human, wherein the disease or conditions is an autoimmune disease, inflammation, a lymphoproliferative disease, arthritis, asthma, restenosis of vessels such as arteries following angioplasty, or cancer.

Another object of the present invention is to provide a composition and method effective to treat cancer.

Another object of the present invention is to provide a composition that is simple to prepare.

Another object of the present invention is to provide a composition that is minimally toxic to the recipient.

These and other objects, features and advantages of the present invention will become apparent after a review of the following detailed description of the disclosed embodiment and the appended claims.

DETAILED DESCRIPTION OF THE INVENTION

The present invention provides novel synthetic oligonucleotide sequences and methods of using them. These novel synthetic oligonucleotide sequences (hereinafter sequence) of 3 to 9 bases in length comprise one or more non-DNA bases comprising one or more nebularine bases, one or more hypoxanthine bases, or one or more uracil bases, or combinations of nebularine, hypoxanthine and uracil bases. These sequences may optionally further comprise one or more guanine bases or one or more thymine bases, or combinations thereof. Preferably the guanine and thymine bases are phosphodiester bases. One or more of these sequences may be combined with an acceptable carrier, such as a pharmaceutically acceptable carrier, to form a composition. Further, these compositions may be combined with one or more known therapeutic agents.

These compositions are useful in inducing a cellular response. In one embodiment, a composition comprising a sequence and a pharmaceutically acceptable carrier is administered to an animal or human, in an amount effective to induce a cellular response in the animal or human. In one embodiment, the cellular response is inhibition of cellular proliferation, induction of cell cycle arrest or induction of apoptosis. In a preferred embodiment, the cells are cancer cells.

The compositions of the present invention may be used to treat diseases or conditions characterized by undesired cellular proliferation.

In a preferred embodiment, a composition comprising a sequence and a pharmaceutically acceptable carrier is administered to an animal or human having cancer in an amount effective to treat the cancer in the animal or human. The unexpected ability of these sequences to induce a cellular response such as inhibition of cellular proliferation, induction of cell cycle arrest or induction of apoptosis addresses a long felt unfulfilled need in the medical arts and provides an important benefit for animals and humans.

The following notation is used to describe the sequence of bases in the oligonucleotides sequences of the present invention: G=Guanine; I=Hypoxanthine; Neb=Nebularine; T=Thymine; and, U=Uracil. As used herein, sequence refers to a synthetic oligonucleotide comprising at least one of the bases I, N or U, or combinations thereof, further optionally containing at least one of the bases G or T, or combinations thereof. The sequence is preferably 3 to 9 bases in length.

As used herein, response refers to induction of a cellular response. Any cell may be chosen and include without limitation cancer cells, immune cells, synovial cells and endothelial cells. A preferred cell for induction of a cellular response is a cancer cell.

As used herein, the phrases "therapeutic treatment" and "amount effective to" refer to an amount of a sequence effective induce a cellular response, including but not limited to inhibition of cellular proliferation, arrest of cell cycle progression, or induction of apoptosis.

As used herein, the word "response" refers to inhibition of proliferation, induction of cell cycle arrest, or induction of apoptosis, in cells.

As used herein, the phrase "effective in responsive cells" refers to the ability of the sequence to cause a response in a cell, including but not limited to inhibition of proliferation, induction of cell cycle arrest, or induction of apoptosis.

As used herein, the phrases "therapeutic treatment", "effective amount" and "amount effective to" refer to an amount of a sequence effective to cause a response in a cell or to treat a disease or condition characterized by undesired cellular proliferation.

As used herein, the phrase "chemotherapeutic" is any agent approved by a regulatory agency of a country or state government or listed in the U.S. Pharmacopoeia or other generally recognized pharmacopoeia to treat disease in an animal or human, particularly cancer.

As used herein, the word "disease" relates to a condition wherein bodily health is impaired. Disease and condition are used interchangeably throughout this application.

As used herein, the word "antineoplastic" refers to preventing the development, maturation, proliferation or spread of cancer cells.

Administration of a composition comprising an effective amount of a sequence of the present invention and an acceptable carrier to an animal or human, is a therapeutic treatment that prevents, treats or eliminates a disease or condition including, but not limited to, cancer, arthritis, lymphoproliferative disorders, inflammation, asthma, and restenosis of vessels such as arteries following angioplasty. Cancers include, but are not limited to, squamous cell carcinoma, fibrosarcoma, sarcoid carcinoma, melanoma, mammary cancer, lung cancer, colorectal cancer, renal cancer, osteosarcoma, cutaneous melanoma, basal cell carcinoma, pancreatic cancer, bladder cancer, brain cancer, ovarian cancer, prostate cancer, leukemia, lymphoma and metastases derived therefrom. Forms of arthritis include, but are not limited to, juvenile arthritis, osteoarthritis and rheumatoid arthritis.

The therapeutic effectiveness of these sequences may be increased by methods including, but not limited to, chemical modification of bases, sugars or phosphate backbone, chemical supplementation, biotechnological amplification of sequences using bacterial plasmids containing the appropriate sequences, complexing to biological or chemical carriers, or coupling the sequences to tissue-type or cell-type directed ligands or antibodies.

Compositions comprising one or more sequences and a pharmaceutically acceptable carrier are prepared by uniformly and intimately bringing into association the sequence and the pharmaceutically acceptable carrier. The terms "pharmaceutically acceptable carrier" or "pharmaceutically acceptable vehicle" are used herein to mean, without limitation, any liquid, solid or semi-solid, including, but not limited to, water or saline, a gel, cream, salve, solvent, diluent, fluid ointment base, ointment, paste, implant, liposome, micelle, giant micelle, and the like, which is suitable for use in contact with living animal or human tissue without causing adverse physiological responses, and which does not interact with the other components of the composition in a deleterious manner. Other pharmaceutically acceptable carriers or vehicles known to one of skill in the art may be employed to make compositions for delivering the oligonucleotide sequences of the present invention. Liquid carriers are aqueous carriers, non-aqueous carriers or both and include, but are not limited to, aqueous suspensions, dimethyl sulfoxide, ethanol, oil emulsions, water in oil emulsions, water-in-oil-in-water emulsions, site-specific emulsions, long-residence emulsions, sticky-emulsions, microemulsions and nanoemulsions. Solid carriers are biological carriers, chemical carriers or both and include, but are not limited to, viral vector systems, particles, microparticles, nanoparticles, microspheres, nanospheres, minipumps, bacterial cell wall extracts and biodegradable or non-biodegradable natural or synthetic polymers that allow for sustained release of the sequences. Emulsions, minipumps and polymers can be implanted in the vicinity of where delivery is required. Methods used to complex a sequence(s) to a solid carrier include, but are not limited to, direct adsorption to the surface of the solid carrier, covalent coupling to the surface of the solid carrier, either directly or via a linking moiety, and covalent coupling or electrostatic coupling to the polymer used to make the solid carrier. Optionally, a sequence(s) can be stabilized by the addition of non-ionic or ionic polymers such as polyoxyethylenesorbitan monooleates (Tweens), hyaluronic acid or aluminum hydroxide. Other carriers known to one of ordinary skill in the art may be employed.

Preferred aqueous carriers include, but are not limited to, water, saline and pharmaceutically acceptable buffers. Preferred non-aqueous carriers include, but are not limited to, a mineral oil or a neutral oil including, but not limited to, a diglyceride, a triglyceride, a phospholipid, a lipid, an oil and mixtures thereof, wherein the oil contains an appropriate mix of polyunsaturated and saturated fatty acids. Examples include, but are not limited to, soybean oil, canola oil, palm oil, olive oil and miglyol, wherein the fatty acids can be saturated or unsaturated. Optionally, excipients may be included regardless of the pharmaceutically acceptable carrier used to present the sequence to the responding cells. These excipients include, but are not limited to, anti-oxidants, buffers, and bacteriostats, and may include suspending agents and thickening agents.

The sequences of the present invention may be combined with pharmaceutically acceptable carriers and administered as compositions in vitro or in vivo. Forms of administration include, but are not limited to, injections, solutions, creams, gels, implants, pumps, ointments, emulsions, suspensions, microspheres, particles, microparticles, nanoparticles, liposomes, pastes, patches, tablets, transdermal delivery devices, sprays, aerosols, or other means familiar to one of ordinary skill in the art. Such pharmaceutically acceptable carriers are commonly known to one of ordinary skill in the art. Pharmaceutical formulations of the present invention can be prepared by procedures known in the art using well known and readily available ingredients. For example, the compounds can be formulated with common excipients, diluents, or carriers, and formed into tablets, capsules, suspensions, powders, and the like. Examples of excipients, diluents, and carriers that are suitable for such formulations include the following: fillers and extenders (e.g., starch, sugars, mannitol, and silicic derivatives); binding agents (e.g., carboxymethyl cellulose and other cellulose derivatives, alginates, gelatin, and polyvinylpyrrolidone); moisturizing agents (e.g., glycerol); disintegrating agents (e.g., calcium carbonate and sodium bicarbonate); agents for retarding dissolution (e.g., paraffin); resorption accelerators (e.g., quaternary ammonium compounds); surface active agents (e.g., cetyl alcohol, glycerol monostearate); adsorptive carriers (e.g., kaolin and bentonite); emulsifiers; preservatives; sweeteners; stabilizers; coloring agents; perfuming agents; flavoring agents; lubricants (e.g., talc, calcium and magnesium stearate); solid polyethyl glycols; and mixtures thereof.

The formulations can be so constituted that they release the active ingredient only or preferably in a particular location, possibly over a period of time. Such combinations provide yet a further mechanism for controlling release kinetics. The coatings, envelopes, and protective matrices may be made, for example, from polymeric substances or waxes.

One or more sequences may be administered alone, or in combination with other therapeutic modalities including, but not limited to, chemotherapeutic agents, immunotherapeutic agents, antimicrobial agents, antiviral agents or in combination with radiation therapy. Chemotherapeutic agents include, but are not limited to, anti-metabolites, DNA damaging, microtubule destabilizing, microtubule stabilizing, actin depolymerizing, growth inhibiting, topoisomerase inhibiting, HMG-CoA inhibiting, purine inhibiting, pyrimidine inhibiting, metalloproteinase inhibiting, CDK inhibiting, angiogenesis inhibiting, differentiation enhancing and immunotherapeutic agents. Anti-arthritic agents include, but are not limited to, anti-inflammatory, anti-metabolites, pro-apoptotic, DNA damaging, microtubule destabilizing, microtubule stabilizing, actin depolymerizing, growth inhibiting, topoisomerase inhibiting, purine inhibiting, pyrimidine inhibiting, metalloproteinase inhibiting, CDK inhibiting, and angiogenesis inhibiting agents.

Routes of administration are known to one of ordinary skill in the art and include, but are not limited to, oral (e.g. buccal or sublingual), rectal, as a suppository, topical, parenteral, subcutaneous, transdermal, sub-dermal, intramuscular, intraperitoneal, intravesicular, intraarticular, intravenous, intradermal, intracranial, intralesional, intrathecal, intratumoral, intraocular, aerosol, intrapulmonary, intraspinal, intraprostatic, sublingual, placement within cavities of the body, nasal inhalation, pulmonary inhalation, impression into the skin and electroporation, intrauterine, vaginal, into a body cavity, surgical administration at the location of a tumor or internal injury, directly into tumors, into the lumen or parenchyma of an organ, and into bone marrow. Techniques useful in the various forms of administrations mentioned above include but are not limited to, topical application, ingestion, surgical administration, injections, sprays, transdermal delivery devices, osmotic pumps, electrodepositing directly on a desired site, or other means familiar to one of ordinary skill in the art. Sites of application can be external, such as on the epidermis, or internal, for example a gastric ulcer, a surgical field, or elsewhere.

The compositions of the present invention can be applied in the form of creams, gels, solutions, suspensions, liposomes, particles, or other means known to one of skill in the art of formulation and delivery of the compositions. Ultrafine particle sizes can be used for inhalation delivery of therapeutics. Some examples of appropriate formulations for subcutaneous administration include but are not limited to implants, depot, needles, capsules, and osmotic pumps. Some examples of appropriate formulations for vaginal administration include but are not limited to creams and rings. Some examples of appropriate formulations for oral administration include but are not limited to: pills, liquids, syrups, and suspensions. Some examples of appropriate formulations for transdermal administration include but are not limited to gels, creams, pastes, patches, sprays, and gels. Some examples of appropriate delivery mechanisms for subcutaneous administration include but are not limited to implants, depots, needles, capsules, and osmotic pumps. Formulations suitable for parenteral administration include but are not limited to aqueous and non-aqueous sterile injection solutions which may contain anti-oxidants, buffers, bacteriostats and solutes which render the formulation isotonic with the blood of the intended recipient, and aqueous and non-aqueous sterile suspensions which may include suspending agents and thickening agents. Extemporaneous injection solutions and suspensions may be prepared from sterile powders, granules and tablets commonly used by one of ordinary skill in the art.

Embodiments in which the compositions of the invention are combined with, for example, one or more pharmaceutically acceptable carriers or excipients may conveniently be presented in unit dosage form and may be prepared by conventional pharmaceutical techniques. Such techniques include the step of bringing into association the compositions containing the active ingredient and the pharmaceutical carrier(s) or excipient(s). In general, the formulations are prepared by uniformly and intimately bringing into association the active ingredient with liquid carriers. Preferred unit dosage formulations are those containing a dose or unit, or an appropriate fraction thereof, of the administered ingredient. It should be understood that in addition to the ingredients particularly mentioned above, formulations comprising the compositions of the present invention may include other agents commonly used by one of ordinary skill in the art.

The volume of administration will vary depending on the route of administration. Such volumes are known to one of ordinary skill in the art of administering compositions to animals or humans. Depending on the route of administration, the volume per dose is preferably about 0.001 to 100 ml dose, more preferably about 0.01 to 50 ml dose, and most preferably about 0.1 to 30 ml dose. Preferably, the amount of sequence administered per dose is from about 0.001 to 100 mg/kg, more preferably from about 0.01 to 10 mg/kg and most preferably from about 0.1 to 5 mg/kg. The sequence, combination of sequences, and/or additional therapeutic agents can be administered in a single dose treatment, in multiple dose treatments or continuously infused on a schedule and over a period of time appropriate to the disease being treated, the condition of the recipient and the route of administration. Moreover, the sequence can be administered before, at the same time as or after the administration of the therapeutic agent. The particular sequence and the particular therapeutic agent administered, the amount per dose, and the route of administration should be decided by the practitioner using methods known to those skilled in the art and will depend on the disease or condition being treated, for example the type of cancer, the severity of the cancer, the location of the cancer and other clinical factors such as the size, weight and physical condition of the recipient.

A sequence in combination with therapeutic agent, for example a chemotherapeutic agent, is administered to an animal having cancer or arthritis in an amount effective to enhance the anti-neoplastic effect of a chemotherapeutic agent or the anti-arthritic effect of an anti-arthritic agent. Preferably, the amount of therapeutic agent administered per dose is from about 0.001 to 1000 mg/m$^2$ or from about 0.01 to 1000 mg/kg, more preferably from about 0.01 to 500 mg/m$^2$ or about 0.01 to 500 mg/kg and most preferably from about 0.1 to 100 mg/m$^2$ or about 0.1 to 100 mg/kg. The particular sequence and the particular therapeutic agent administered, the amount per dose, the dose schedule and the route of administration should be decided by the practitioner using methods known to those skilled in the art and will depend on the type of disease, the severity of the disease, the location of the disease and other clinical factors such as the size, weight and physical condition of the recipient. In addition, in vitro assays may optionally be employed to help identify optimal ranges for sequence and for sequence plus therapeutic agent administration. Various assays useful for this purpose are described in PCT CA00/01467 (WO 01/44465), the entirety of which is incorporated herein by reference. Additional assays for evaluation of the efficacy of the sequences of the present invention, and for evaluation of the efficacy of these sequences in combination with other therapeutic agents are described by Oncogene Research Products, P.O. Box 12087, La Jolla, Calif., 92039 (Apoptosis Catalog and Technical Guide 2002–2003, especially pages 5–295) the entirety of which is incorporated herein by reference. Such assays include assays designed to analyze DNA fragmentation, apoptosis, mitochondrial markers, endoplasmic reticulum markers, free nucleosomes, nuclear matrix proteins, detection and activity of numerous caspases and related proteins, including but not limited to caspases 1 through 14, glutathione, superoxide dismutase, members of the bcl-2 family, analysis of the Fas/TNR-R super family, PARP related products, analysis of apoptotic signal transducers, analysis of various signaling receptors including death receptors, Apo2, decoy receptors, analysis of apoptotic membrane proteins, nervous system apoptotic markers, numerous markers for cell cycle and cellular proliferation, mitotic kinases, bromodeoxyuridine assays, and p53 assays. The evaluation of the efficacy of the sequences of the present invention may also be evaluated in terms of other agents, and therapeutic agents, such as inducers of apoptosis and cell synchronization reagents as described by Oncogene Research Products, P.O. Box 12087, La Jolla, Calif., 92039 (Apoptosis Catalog and Technical Guide 2002–2003, especially pages 99–104 and pages 214–255, the entirety of which is incorporated herein by reference). Such agents include but are not limited to actinomycin D, amphidocolin, A23187, caffeine, camptothecin, cycloheximide, dexamethasone, doxorubicin, 5-fluorouracil, hydroxyurea, paclitaxel, staurosporine, thymidine, vinblastine, retinoic acid, etoposide, okadaic acid, vincristine and methotrexate.

The following examples will serve to further illustrate the present invention without, at the same time, however, constituting any limitation thereof. On the contrary, it is to be clearly understood that resort may be had to various other embodiments, modifications, and equivalents thereof which, after reading the description herein, may suggest themselves to those skilled in the art without departing from the spirit of the invention.

EXAMPLE 1

Preparation of Sequences

Sequences were prepared by Sigma-Genosys (Woodlands, Tex., USA). Nebularine (2'deoxyNebularine), inosine and uracil phosphoramidites were purchased from Glen Research, Sterling, Va., USA. The sequences were dispersed in autoclaved deionized water or in a pharmaceutically acceptable buffer such as, but not limited to, saline immediately prior to use.

EXAMPLE 2

Cells

Human Jurkat T cell leukemia cells were obtained from the American Type Culture Collection (Rockville, Md.). The Jurkat T cells were maintained RPMI 1640 medium, supplemented with 10% heat-inactivated (56° C., 30 min) fetal bovine serum (all from Sigma Aldrich, Canada) in an atmosphere of 5% $CO_2$ at 37° C. Cells were seeded at $2 \times 10^5$ cells/ml medium in 6-well flat-bottomed tissue culture plates and incubated with the sequences of the present invention.

EXAMPLE 3

Induction of Apoptosis by Sequences Containing Nebularine Bases

Redistribution of plasma membrane phosphatidylserine is a characteristic of cells undergoing apoptosis (Martin et al., J. Exp. Med., 182:1545, 1995). The redistribution of phosphatidylserine in the plasma membrane during apoptosis was measured by flow cytometry using FITC-conjugated annexin V (BD Pharmingen, San Diego, Calif.). Jurkat T cell leukemia cells were incubated at $2.5 \times 10^5$ cells/ml for 48 hours with 53.0 µM of the sequences of the present invention. The percentage of cells in apoptosis after exposure to sequences was reported in Table 1. The percentage of apoptosis in untreated Jurkat T cell leukemia cells was 5%.

TABLE 1

Percentage of positive cells for phosphatidylserine (cells in apoptosis) in Jurkat T cell leukemia cells treated with compositions of the present invention

| Sequences (number of bases) | % Cells in Apoptosis |
| --- | --- |
| NebTNeb-(3) | 14 |
| GNebG-(3) | 47 |
| NebNebGNebNebNeb-(6) | 16 |
| NebNebNebNebNeb-(6) | 6 |
| NebNebNebTNebNeb-(6) | 5 |
| GGGNebGG-(6) | 52 |
| GGGTNebG-(6) | 60 |
| GGNebNebGG-(6) | 48 |
| GGNebTGG-(6) | 45 |
| NebGGTGG-(6) | 52 |
| NebGGTGNeb-(6) | 58 |
| GGGTGGNeb-(7) | 54 |
| NebGGGTGG-(7) | 62 |

As shown in Table 1, all the sequences except NebNebNebNebNeb and NebNebNebTNebNeb induced apoptosis of Jurkat T cell leukemia cells.

EXAMPLE 4

Inhibition of Cell Proliferation, Cell Cycle Arrest and Induction of Apoptosis by Sequences Containing Hypoxanthine Bases Jurkat T cell leukemia cells were incubated at $2.5 \times 10^5$ cells/ml for 48 hours with several sequences of the present invention. Cell proliferation was measured using dimethylthiazol-diphenyl-tetrazolium (MTT) reduction (Mosman et al. J. Immunol. Methods 65:55, 1983). MTT reduction was measured at a wavelength of 570 nm using a multiple spectrophotometer reader. Cell cycle stage was determined using a commercial kit (CycleTest™ Plus DNA; Becton Dickinson). Accumulation of cells in G0/G1, early (SE), mid (SM), late (SL) or G2/M phases was analyzed by flow cytometry using MODFIT LT software (Verity Software House Inc., Topsham, Mass., USA). The percentage of cells in apoptosis was determined by annexin-V FITC as described in the example 3. Inhibition of cell proliferation, cell cycle arrest and induction of apoptosis after sequence treatment is reported in Table 2.

TABLE 2

Inhibition of proliferation, cell cycle arrest and induction of apoptosis by sequences containing hypoxanthine bases

| SEQUENCES (number of bases) | Cell division: % inhibition | | | Cell cycle block | % cells in apoptosis |
| --- | --- | --- | --- | --- | --- |
| Dose (µM) | 0.53 µM | 5.3 µM | 53.0 µM | 53.0 µM | 53.0 µM |
| GGITGG-(6) | 7 | 17 | 35 | SE | 39 |
| GGGIGG-(6) | 5 | 8 | 26 | No cell cycle arrest | 25 |
| IIGTII-(6) | 6 | 7 | 46 | No cell cycle arrest | 59 |
| IGGGTGG-(7) | 3 | 12 | 38 | SE | 52 |
| GGGTGGI-(7) | 4 | 13 | 38 | SE | 54 |
| IGGGTGGI-(8) | 3 | 11 | 29 | SM | 60 |
| GGGTGGIII-(9) | 8 | 8 | 19 | SL | 63 |
| GIG-(3) | n.d. | n.d. | n.d. | n.d. | 36 | n.d. = not determined

As shown in Table 2, all these sequences either inhibited cell proliferation, arrested the cell cycle or induced apoptosis of Jurkat T cell leukemia cells.

EXAMPLE 5

Inhibition of Cell Proliferation, Cell Cycle Arrest and Induction of Apoptosis by Sequences Containing Uracil Bases Jurkat T cell leukemia cells were incubated at $2.5 \times 10^5$ cells/ml for 48 hours with sequences. Inhibition of proliferation was measured by MTT reduction, cell cycle arrest by CycleTest™ Plus DNA kit and apoptosis was determined by annexin-V FITC as described in the example 3. Inhibition of cell proliferation, cell cycle arrest and induction of apoptosis after sequence treatment was reported in Table 3.

TABLE 3

Inhibition of proliferation, cell cycle arrest and induction of apoptosis by sequences containing uracil bases

| SEQUENCES (number of bases) | Cell division: % inhibition | | | Cell cycle block | % cells in apoptosis |
|---|---|---|---|---|---|
| Dose (μM) | 0.53 μM | 5.3 μM | 53.0 μM | 53.0 μM | 53.0 μM |
| GGUTGG-(6) | 9 | 25 | 41 | SE | 36 |
| GGGUGG-(6) | 8 | 17 | 39 | SE | 32 |
| UUGTUU-(6) | 5 | 11 | 30 | SL/G2M | 72 |
| UGGGTGG-(7) | 3 | 18 | 41 | SE | 44 |
| GGGTGGU-(7) | 7 | 31 | 47 | SE | 51 |
| UGGGTGGU-(8) | 5 | 25 | 46 | SE | 51 |
| GGGTGGUUU-(9) | 7 | 16 | 41 | SE | 63 |
| GUG-(3) | n.d. | n.d. | n.d. | n.d. | 31 | n.d. = not determined

As shown in Table 3, all these sequences either inhibited cell proliferation, arrested the cell cycle or induced apoptosis of Jurkat T cell leukemia cells.

All patents, publications and abstracts cited above are incorporated herein by reference in their entirety. It should be understood that the foregoing relates only to preferred embodiments of the present invention and that numerous modifications or alterations may be made therein without departing from the spirit and the scope of the present invention as defined in the following claims.

We claim:

1. A composition comprising a synthetic oligonucleotide sequence of 6–9 bases in length, comprising at least one nebularine base, wherein the sequence comprises NebGGT-GNeb.

2. A composition comprising a synthetic oligonucleotide sequence of 6–9 bases in length, comprising at least one hypoxanthine base, wherein the sequence comprises IIGTII.

3. A composition comprising a synthetic oligonucleotide sequence of 6–9 bases in length, comprising at least one uracil base, wherein the sequence comprises UUGTUU.

* * * * *